(12) United States Patent
Pelz

(10) Patent No.: US 7,225,663 B2
(45) Date of Patent: Jun. 5, 2007

(54) APPARATUS FOR MEASURING GREEN-SPEED

(76) Inventor: David T. Pelz, 1310 Ranch Rd. 620, South, Suite B-1, Austin, TX (US) 78734

( * ) Notice: Subject to any disclaimer, the term of this patent is extended or adjusted under 35 U.S.C. 154(b) by 243 days.

(21) Appl. No.: 11/052,102

(22) Filed: Feb. 8, 2005

(65) Prior Publication Data
US 2005/0145011 A1   Jul. 7, 2005

Related U.S. Application Data

(63) Continuation-in-part of application No. 10/161,592, filed on Jun. 5, 2002, now Pat. No. 6,860,139.

(51) Int. Cl.
*G01N 3/56* (2006.01)

(52) U.S. Cl. ............................................................. 73/9
(58) Field of Classification Search ...................... 73/9; 473/404
See application file for complete search history.

(56) References Cited

U.S. PATENT DOCUMENTS

| 3,215,436 A | 11/1965 | Carter |
| 3,802,895 A | 4/1974 | Dahlgren et al. |
| 6,547,680 B1 | 4/2003 | Marchese, Jr. |
| 6,749,527 B2 * | 6/2004 | Hughes ..................... 473/404 |
| 2004/0097303 A1 | 5/2004 | Hughes |

* cited by examiner

Primary Examiner—Robert Raevis
(74) Attorney, Agent, or Firm—Welsh & Flaxman LLC

(57) ABSTRACT

A method and apparatus is employed in determining the green-speed of a golf putting green. The method is achieved by selecting a site on a putting green having a relatively flat surface and determining the extent of putting surface available for measurements, setting a green-speed reading apparatus including a ramp, which includes a raised start end and a ground contacting release end with at least one golf ball rolling track thereon, in a first direction whereby the release end of the ramp contacts the putting green surface at the selected site, selecting one of two predetermined start positions for a golf ball based upon the extent of putting surface available for measurements and retaining the golf ball at the selected start position in the track, the start position being at the raised start end of the track, releasing the golf ball from the start position, allowing the golf ball to roll down the track by gravity onto the putting green surface, measuring the distance the golf ball rolls across the putting green from the release end of the ramp, repeating the test with the apparatus facing in the opposite direction at the selected site and measuring the distance the golf ball rolls across the putting green from the release end of the ramp, and calculating the average distance of all the golf balls rolled to determine a value in terms of green-speed.

18 Claims, 5 Drawing Sheets

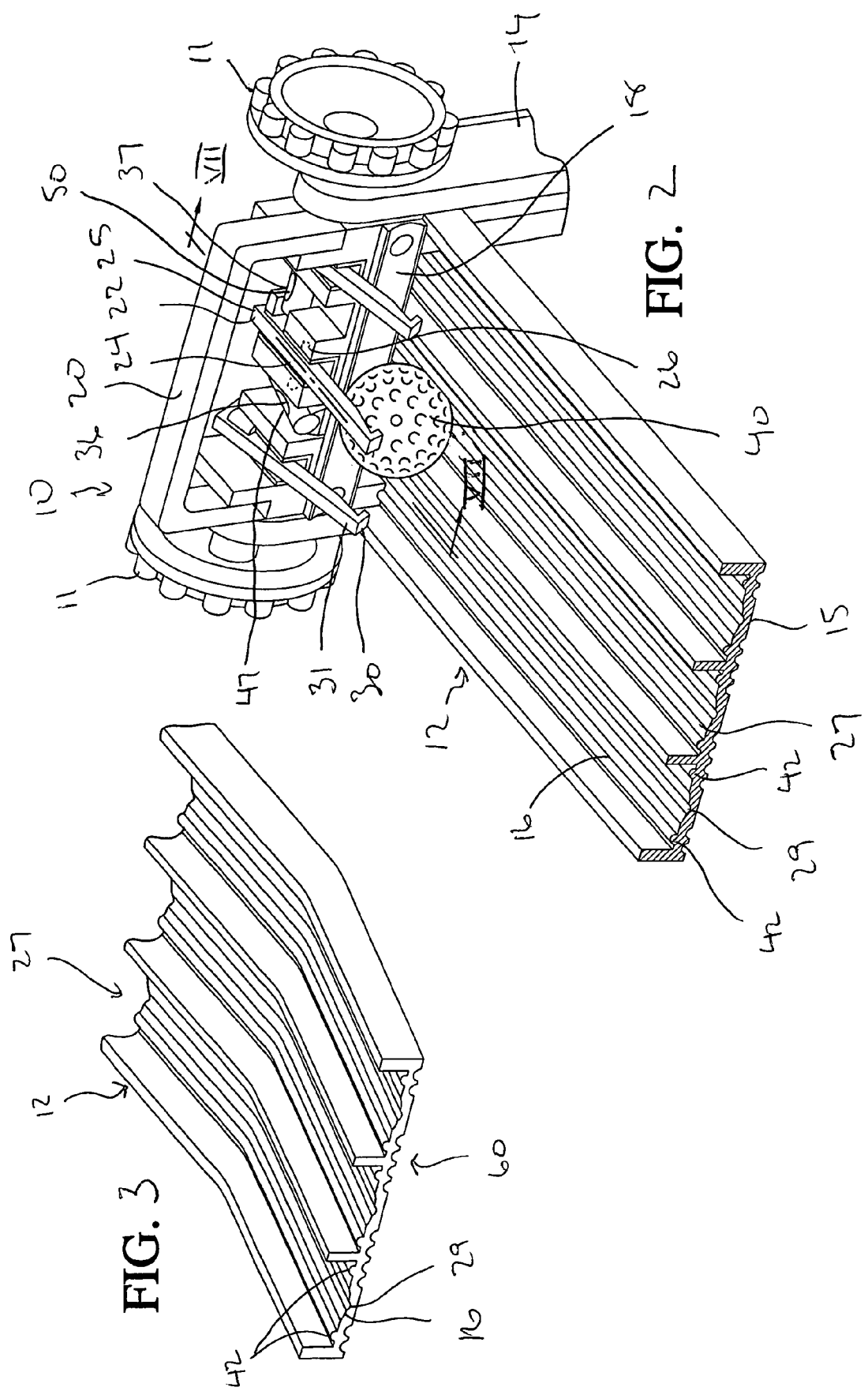

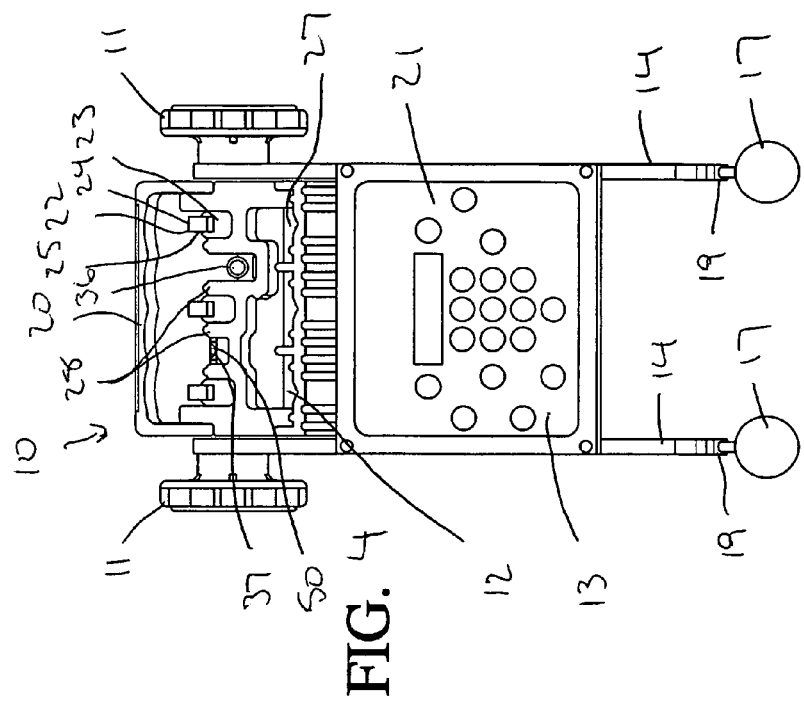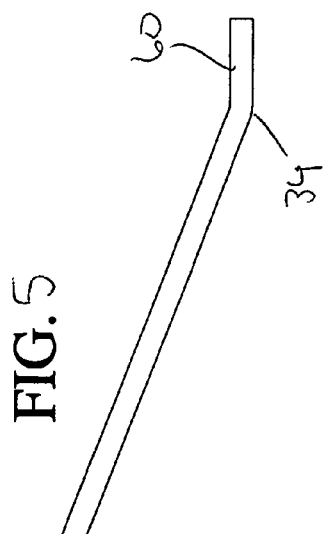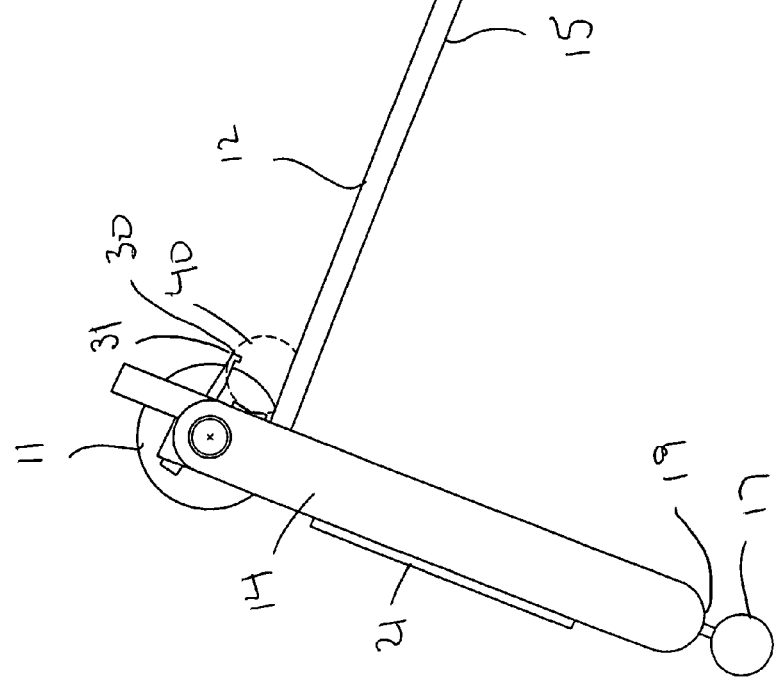

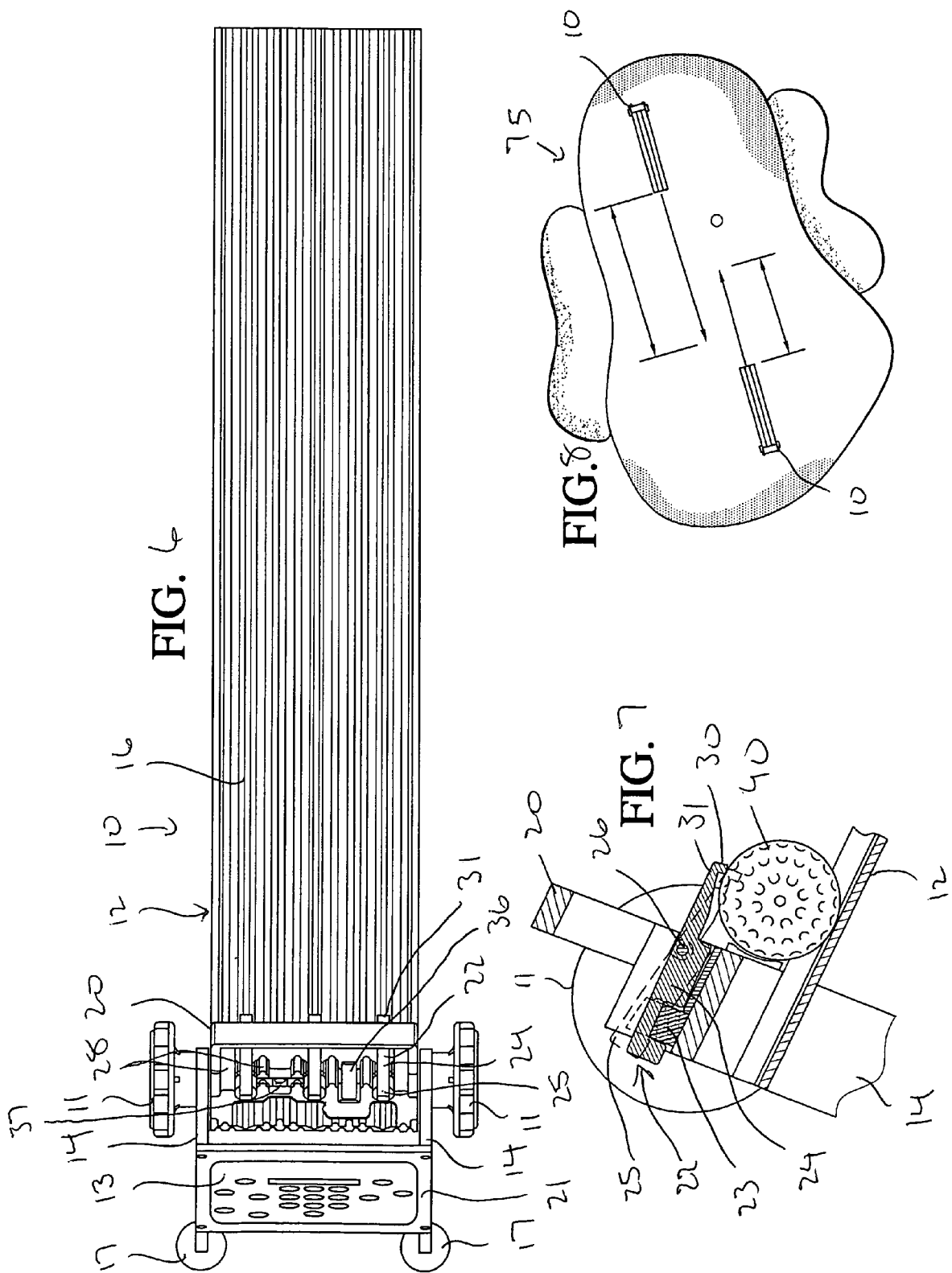

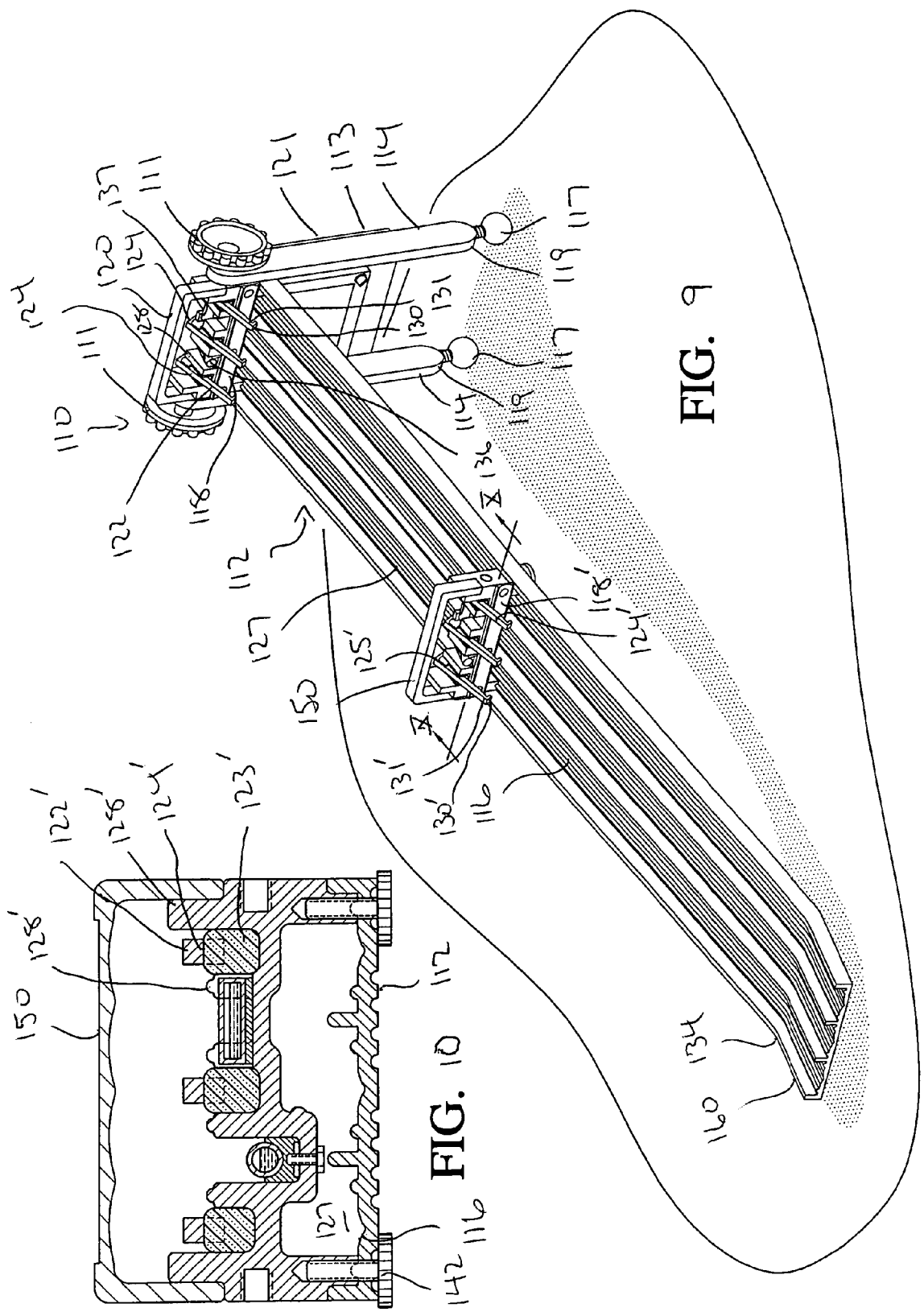

APPARATUS FOR MEASURING GREEN-SPEED

CROSS REFERENCE TO RELATED APPLICATIONS

This application is a continuation-in-part of U.S. patent application Ser. No. 10/161,592, entitled "APPARATUS FOR MEASURING GREEN SPEED", filed Jun. 5, 2002 now U.S. Pat. No. 6,860,139.

BACKGROUND OF THE INVENTION

1. Field of the Invention

The present invention relates to a method and an apparatus for measuring the "green-speed" of golf course greens. Green-speed more precisely is a measure of distance. It is a quantitative measurement of a green surface characteristic (green-speed), which relates to how far a golf ball rolls after being given a fixed initial speed (e.g. putted from an absolute reference stroke), and then using that quantity for green control, comparison and maintenance purposes. More particularly, the invention relates to an apparatus for measuring the green-speed of putting greens in a precise manner that improves on the current measuring practice.

2. Description of the Prior Art

The speed at which a golf ball rolls across a putting green toward the hole varies from golf course to golf course and sometimes from putting green to putting green on the same golf course. The faster the green-speed, the more skill is required to consistently hole putts in the least number of strokes. Golf course greens which have variations in green-speed between different greens or even differences in green-speed on the same green, require extraordinary skill on the part of the golfer to hole putts and usually result in considerably higher scores.

Ideally all golf greens on the same course are uniform with little variation in green-speed from one green to the next. Variances in green-speeds usually depend upon a wide variety of factors including maintenance procedures, grass types, weather conditions, number of rounds of golf played on the golf course and the skill level of golfers using the golf course, among others. For example, public golf courses with a large number of rounds and with a relatively large number of limited skill players tend to have green-speeds that are slow (between 6-8). Most upscale public golf courses and private golf clubs have greens with somewhat faster green-speeds (between 8.5-10). Courses that are used for tournament play, particularly professional tournaments, have green-speeds that are considerably faster (between 10.5-14).

Since 1976, in order to aid golf course superintendents to keep green-speeds consistent, and/or to regulate the green-speed for a particular event or playing condition, the green-speed of greens traditionally has been measured using a standard device called a Stimpmeter. This device was developed by Edward Stimpson to provide a standard device to consistently release a number of golf balls, one at a time, at a constant initial energy onto a green, to allow quantitative measurement of green-speed. The Stimpmeter is designed to be used on a wide variety of courses and for a wide variety of green conditions.

The Stimpmeter is a thirty-six inch long, straight aluminum bar with a V-shaped channel along its length, with a milled notch adjacent the upper portion of the V-shaped channel to accommodate a golf ball. The lower end of the Stimpmeter is provided with a beveled edge, which engages the surface of the green. In use, the beveled end of the Stimpmeter is placed on the green surface and a golf ball is placed in the notch. The Stimpmeter is designed so that a golf ball will be released and start to roll down the V-shaped channel when the notch end of the Stimpmeter is raised, by hand, to an angle of approximately 20 degrees, and then held absolutely still once the ball starts to roll down the ramp.

The United States Golf Association (USGA) specifies that to measure green-speed, three balls are sequentially rolled from a Stimpmeter over a relatively flat part of a green, in a first direction and the average roll distance measured. The test is repeated with the balls rolling over the same area, in the opposite direction. The average distance of all six rolls then represents the green-speed. This USGA specified Stimpmeter measurement has been the standard for many years and is recognized, not only by golf course superintendents, but also by the various local, national and international golf associations.

The design of the Stimpmeter often produces a number of inaccuracies in green-speed measurement. The release height of a golf ball placed in the notch in the V-shaped channel depends upon the dimple configuration and exact placement position of the golf ball relative to the edge of the notch. This causes errors in the initial speed of release of balls onto the green surface, which in turn, cause direct errors in green-speed measurements. Operator error, such as lifting or raising the bar in a jerky motion or not holding the bar steady as the ball rolls during a test may also cause a relatively large variation in roll distance. The flat sides of the V-shaped channel often causes golf balls rolling on dimple flats to chatter and bounce against the sides of the channel, which also affects roll distance. Because balls impact the green surface at the lower end of the Stimpmeter at a 20 degree angle, they bounce, thereby creating further variables in roll distance. Three balls are used, each rolled from the same spot in the same direction, and frequently a ball roll track is formed in the grass on the green, causing roll distances to be erroneously longer with each successive ball rolled in a previous ball track. Still further, the Stimpmeter is unable to detect slopes in the surface of the greens to be measured.

The prior art, other than the Stimpmeter, is mostly silent with respect to devices for reading green-speed.

U.S. Pat. No. 3,215,436 to Carter, directed to a green surface, shows a green-speed measuring device with a V-shaped ball channel supported at an angle of 30 degrees on a tripod support. The lower end of the track is formed with curved extensions tapering to a point. A golf ball is released down the channel. The distance the ball rolls is used to create a coefficient of putting friction that represents the green-speed of the putting surface.

U.S. Pat. No. 5,358,446 to Bergman shows a ramp used to roll a bowling ball with a lower forward rail portion, which is horizontal to the alley surface.

As such, and as those skilled in the art will certainly appreciate, a need exists for an improved mechanism for consistently and reliably measuring green speed in a variety of environments. The present invention provides such an apparatus.

SUMMARY OF THE INVENTION

The green-speed measuring apparatus of the present invention represents an improvement over the conventional Stimpmeter, green-speed measuring device. The present invention provides a green-speed reading apparatus that provides more accurate and consistent readings with less errors.

The green-speed measuring apparatus includes a three track ramp for rolling three golf balls along parallel, but distinct tracks over the surface of a green being tested. The ramp is raised above the putting surface to a precise 20.2 degree angle relative to the local horizontal using a preconfigured angled level-vial and an adjustable-length leg structure, which mechanically supports the upper start end of the ramp at a fixed position. The local horizontal is defined as a plane perpendicular to the local gravitational vertical vector. Each golf ball sits in a radiused rolling groove against a radiused ball stop and is held in a pre-release starting position by a release trigger holding plate, which is also radiused to hold golf balls in a repeatable position, regardless of ball surface dimple location or size. The ramp has three ball-radiused rolling grooves, which reduce golf ball chatter when a dimpled surface ball tolls down the grooves. The end of the ramp is curved in order to release golf balls horizontally so as to be essentially parallel to the putting green surface thereby minimizing or totally eliminating ball bounce as the ball impacts the surface of the green.

Other features of the apparatus include a level-vial to accurately determine the 20.2 degree release angle, relative to the local horizontal, to give all balls the same initial energy and speed. A flat bottom surface which works with second level-vial to determine side-to-side slope (cross slopes). The release trigger has a holding plate to accurately and consistently grip a golf ball in the same starting position height, regardless of surface dimple size or location prior to each test.

Among the objects of the present invention is the provision of a green-speed measuring apparatus that represents an improvement of the conventional Stimpmeter green-speed measuring device.

A further object of the present invention is a green speed measuring apparatus that may be used where limited space for measuring is an issue.

Another object of the present invention is the provision of a green reading method and apparatus that provides more accurate and consistent readings of green-speed.

Still another object of the present invention is the provision of a green-speed measuring method and apparatus that provides a roll ramp, which is precisely located at the same, release angle relative to the local horizontal each time a golf ball is used to test the green-speed of a golf green.

Another object of the present invention is the provision of a green-speed measuring method and apparatus that has three independent rolling grooves resulting in three different and parallel ball tracks on the putting surface.

An additional object of the present invention is the provision of a green-speed measuring method and apparatus which has a rolling ramp with a curved lower surface, which releases a golf ball horizontal onto a putting green surface, in order to minimize or eliminate ball bounce when the test balls are released.

Still another object of the present invention is the provision of a green-speed measuring method and apparatus, which has a precise ball release mechanism to promote more consistent rolls for more accurate results.

Yet another object of the present invention is to provide ball-radiused tracks in the ramp to aid in reducing ball chatter.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a detailed perspective view of the trigger mechanism of the green-speed measurement device shown in FIG. 1.

FIG. 3 is a detailed perspective view of the release end of the green-speed measurement device shown in FIG. 1.

FIG. 4 is a rear plan view thereof.

FIG. 5 is a side plan view thereof.

FIG. 6 is a top plan view thereof FIG. 7 is a cross sectional view along the line VII-VII in FIG. 2.

FIG. 8 is a schematic of a putting green surface in accordance with the present invention.

FIG. 9 is a perspective view in accordance with an alternate embodiment.

FIG. 10 is a cross sectional view along the line X-X in FIG. 9.

DESCRIPTION OF THE PREFERRED EMBODIMENTS

Figure 1:
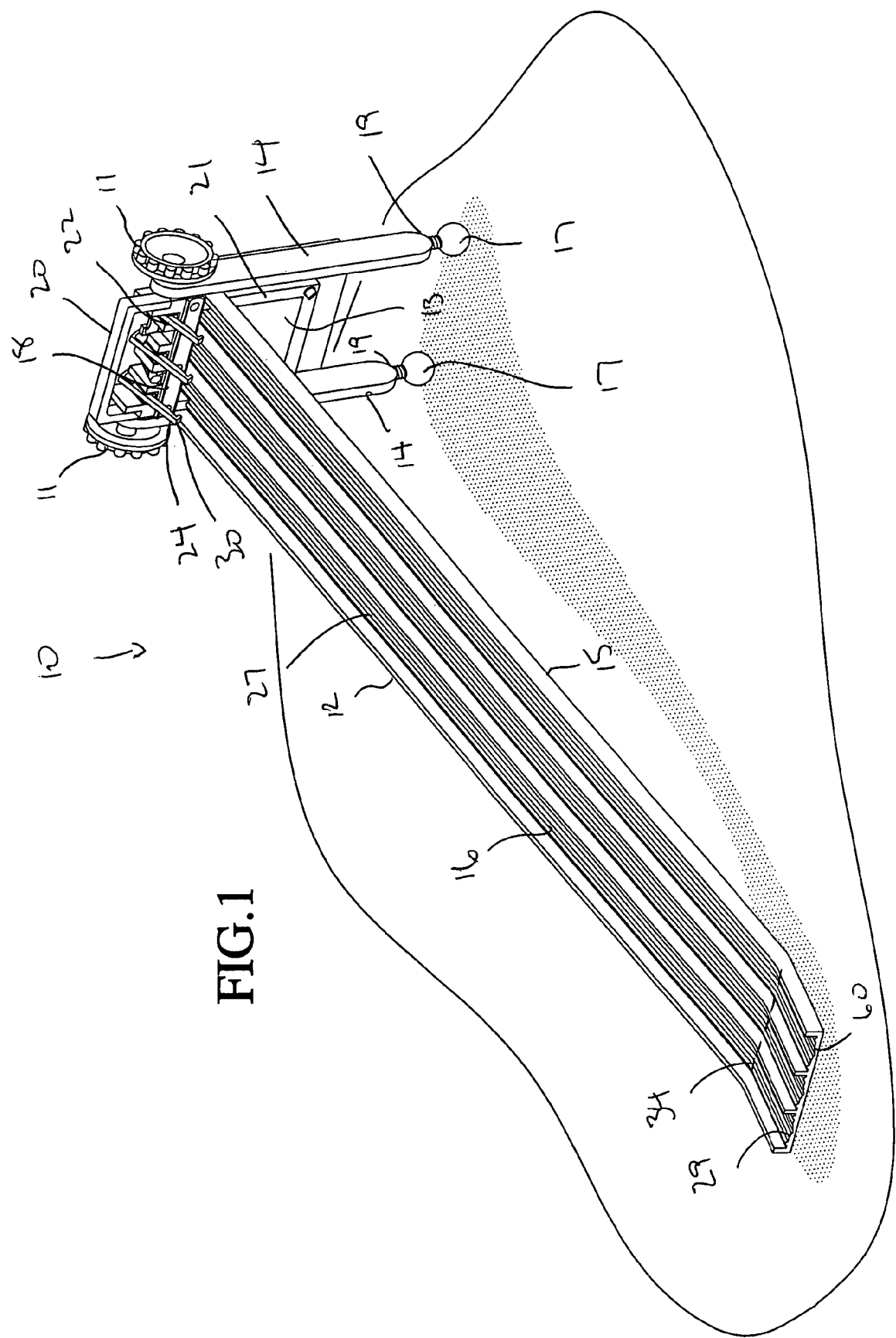
FIG. 1 is a perspective view of the green-speed reading apparatus of the present invention.

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

Referring to FIGS. 1 to 7, the green-speed reading apparatus 10 of the present invention is disclosed. The apparatus 10 is composed of a golf ball rolling ramp 12 supported above a green surface 75 at an angle of 20.2 degrees (in the test position) with a pair of spaced legs 14. The legs 14 are spaced by a cross bar 21 (which in accordance with this embodiment includes a calculator 13 positioned between the spaced legs 14) and are pivotally and removably secured to the ramp 12 by threaded knobs 11.

The legs 14 pivot when the knobs 11 are loosened such that the legs 14 may be selectively folded onto the top side of the ramp 12 for storage and when the apparatus 10 is used as a site selection aid in the manner discussed below. When the legs 14 are folded over and the cross bar 21 rests on the upper surface of ramp 12, a device with a flat bottom surface 15 is created. This allows one to use the flat bottom surface 15 of the apparatus 10 for measuring putting green slopes as described hereinbelow.

The legs 14 include castors 17 which are respectively screwed into the bottom 19 of each leg 14 and are adjustable so the overall length of the legs 14 may be varied to accommodate variations or imperfections in the surface of a putting green surface 75 being measured. As those skilled in the art will certainly appreciate, other leg adjustment mechanism may be employed without departing from the spirit of the present invention.

The ramp 12 is formed with three parallel, golf ball rolling tracks 27 in the form of grooves 16 extending the entire length of the ramp 12. In accordance with a preferred embodiment of the present invention, these grooves 16 are milled with a radius compatible with the outside dimensions of a golf ball 40 and present a smooth rolling surface to dimpled golf balls 40 having a standard 1.68 inch diameter. This structure reduces chatter and allows the balls 40 to roll true, as opposed to bouncing on the dimples of the balls 40, as the golf balls 40 roll down the respective grooves 16 toward the green surface 75. If the grooves were V-shaped the balls would chatter as they bounced when the dimples contacted the edges of the V-shaped groove. Because three separate rolling grooves 16 are provided, the golf balls 40 toll on three distinctly different parts of the putting green surface 75 and produce three separate, distinctly different ball tracks which eliminate the inconsistencies in rolling distance when three balls roll along the same track.

More particularly, each of the grooves 16 includes a central recess 29 extending longitudinally within the center of the groove 16. The rolling characteristics of the balls 40 within the grooves 16 is enhanced by the use of these longitudinally extending central recesses 29 which center the balls 40 as they roll down the ramp 12. The grooves 16 are further provided with side rails 42 positioned along the edges of the grooves 16. The side rails 42 help to maintain the balls 40 within the center of the grooves 16.

In the test position, each golf ball 40 sits in one of the radiused rolling grooves 16 and rests against a radiused backstop 18 on the trigger support block 20. The trigger support block includes plurality of trigger mechanisms 22 (three in accordance with a preferred embodiment of the present invention). Each trigger mechanism 22 is formed with a trigger arm 24 mounted on a pivot rod 26 pivotally movable on upright supports 28 of the trigger support block 20. The front end 31 of the trigger mechanism 22 is formed with a ball holder 30 integrally formed along the front end 31 of the trigger arm 24. The ball holder 30 is contoured to contact the exact top of a golf ball 40 when it is properly seated in the groove 16 and against the radiused backstop 18.

The ball holder 30 of the trigger arm 24 is biased against the golf ball 40 by a resilient spring or sponge-like material 23 placed on the trigger support block 20 at the rear end 25 of trigger arm 24. Therefore, when the rear end 25 of the trigger arm 24 is depressed against the resilient material 23, the front end 31 of trigger arm 24 will raise and the golf ball 40 begins to roll down the ramp 12.

The lower, forward or release end 60 of the ramp 12 is curved beginning just after slope-line 34 so as to lie horizontal and parallel to the local horizontal and the putting green surface 75 when the apparatus 10 is in the test position. The curved forward end 60 (i.e., from the slope line 34 to the very end of the ramp 12) of the ramp 12 releases the golf balls 40 horizontally to the putting surface 75 thereby eliminating or minimizing bounce as the golf balls 40 impact the putting green surface 75.

In accordance with a preferred embodiment of the present invention, two level-vials 36, 37 are mounted on the trigger support block 20. The first level-vial 36 is preconfigured at an angle of 20.2 degrees relative to the horizontal. Thus, when the bubble 47 of the first level-vial is located between the window lines 33, the angle of the ramp 12 relative to the local horizontal is known to be at 20.2 degrees and the apparatus 10 is known to be at the proper height.

The second level-vial 37 assists in determining if cross slopes exist when the apparatus 10 is placed at a selected site. When green-speed testing begins, it is desirable to select a site with no cross slope and as little fall line slope as possible. Thus, the flat bottom surface 15 of the ramp 12 is placed on the selected putting green surface 75 site and slid around until the bubble 50 is located between window lines 51 in the second level-vial 37.

Although U.S. patent application Ser. No. 10/161,592, which is incorporated herein by reference, discloses the use of a third level-vial, the present apparatus does not require such structure and relies upon a preprogrammed calculator 13 preprogrammed to apply Brede's formula to determine green speed. As those skilled in the art will certainly appreciate, Brede's formula is a standard formula used in green speed calculations and states:

$$\text{Green Speed} = 2(A \times B)/(A+B)$$

where,
A is the downhill roll distance, and
B is the uphill roll distance.

Through the application of Brede's formula, minor slope effects are considered in the determination of green speed and are substantially taken out of the green speed equation.

In use, and with reference to FIG. 8, the speed of any area of a putting green, which is either flat or of a constant-slope can be measured. The amount of slope does not matter as long as you roll along the fall-line of the slope (that is, the straight up or downhill direction—no side hill slopes), because the present apparatus 10 takes the effect of gravity out of the green-speed equation (balls gain more roll downhill than they lose rolling uphill, so a straight average of roll distance doesn't work for measuring on sloped surfaces). However, it should be noted that side-hill rolls are never valid for measuring green-speed.

Once you select a site, face the apparatus 10 in the downhill direction and loosen both large leg knobs 11. Adjust the ramp 12 height while watching the first level-vial 36. Snug the large knobs 11 when the first level-vial 36 is approximately centered, and adjust a caster 17 until the cross second level-vial 37 is close to centered. Load a test ball 40 under the trigger arm 24 and release it. Watch carefully from behind the apparatus 10 as the test ball 40 rolls to determine if the apparatus 10 is accurately aimed along the fall-line (straight downhill) direction. If the ball 40 breaks away from a straight-line, adjust the aim of apparatus 10 to be parallel to its final roll direction and release another test ball 40. Roll repeated test balls 40 until one rolls straight down the fall-line. Also, watch the test ball 40 for length of roll. If it rolls far enough to reach a change in slope, move the apparatus 10 further back (up the slope), so as to maintain a constant slope along the entire test area. There is no need to worry about the uphill roll as it will always be within the boundaries of the downhill roll.)

Fine adjust the apparatus 10 by sliding it one-half inch to one side (keeping the ramp 12 parallel to its existing alignment) to prevent any of the "measurement" balls 40 from tracking (rolling) in the exact same path of any test balls 40 previously rolled. Load three balls 40, one under each track trigger arm 24, and make sure all three are against the backstop 18 and centered in their respective tracks 27. Adjust the bubble 50 of the cross-slope second level-vial 37 to be precisely centered, by turning one of the casters 17. Finally, adjust the bubble 47 of the height first level-vial 36 to be perfectly centered (loosen and re-snug the large leg knobs 11).

At this position testing can now begin as the ramp 12 is angled at 20.2 degrees relative to the local horizontal and accurate distance readings can be obtained as each of the balls 40 when released should theoretically roll down the ramp 12 at the same speed under the force of gravity.

Each trigger arm 24 is then gently raised against the pressure of the resilient material 23 and the ball holder 30 is allowed to contact the top surface of each ball 40 to hold the ball 40 in place. Each ball 40 may include a balanced line 41 which is aligned within the slotted window 32 by simply rotating the golf ball 40 to a proper position once the golf ball 40 is retained by the trigger arm 24 and the ball holder 30. When a test is conducted, the rear end 25 of each of the three trigger arms 24 is sequentially pressed causing its associated ball holder 30 to raise and release a golf ball 40 allowing it to roll down a groove 16 on the ramp 12 and onto the green surface 75 in response to the natural effects of gravity. The distance each ball 40 rolls is measured from the end of the ramp 12 to the spot at which the ball 40 came to rest. The test is repeated with the green reading apparatus 10 facing in an opposite direction, rolling the three balls 40 over the same area of the green surface 75. The average of all the distances the balls 40 roll is calculated to determine the green-speed of the green and then adjustments are made for fall line slope and an accurate green-speed distance is recorded and the selected site noted for future tests.

A calculator 13 is provided to assist individuals in performing these calculations. In particular, and as discussed above, the calculator employs Brede's formula in determining green speed. This takes the effect of slope substantially out of the green speed calculation. Ultimately, the two averages obtained during the testing are input and the calculator 13 provides green speed through the application of Brede's formula.

An alternate embodiment in accordance with the spirit of the present invention is disclosed with reference to FIGS. 9 and 10. As those skilled in the art will certainly appreciate, it is often difficult to find a desirable location for taking measurements in view of the fast, highly contoured greens being used on today's golf courses. Specifically, traditional metering devices include ramps requiring substantial distance to accurately perform green speed measurements. The present embodiment overcomes this shortcoming by providing a secondary trigger block positioned midway along the track of the green-speed reading apparatus.

As with the embodiment disclosed with reference to FIGS. 1 to 7, the green-speed reading apparatus 110 is formed of a golf ball rolling ramp 112 supported above a green surface 175 at an angle of 20.2 degrees (in the test position) with a pair of spaced legs 114. The legs 114 are spaced by a cross bar 121 (which in accordance with this embodiment includes a calculator 113 positioned between the spaced legs 114). The legs 114 ate pivotally and removably secured to the tamp 112 by respective threaded knobs 111. The legs 114 include castors 117 which are screwed into the bottom 119 of legs 114 and are adjustable so the overall length of the legs 114 may be varied to accommodate variations or imperfections in the surface of a putting green being measured.

The ramp 112 is formed with three parallel, golf ball rolling tracks 127. The tracks 127 are in the form of grooves 116 extending the entire length of the ramp 112. As with the previous embodiment, these grooves 116 are milled with a radius compatible with the outside dimensions of a golf ball and present a smooth rolling surface to dimpled golf balls having a standard 1.68 inch diameter.

In the test position, each golf ball sits in one of the radiused rolling grooves 116 and rests against a radiused backstop 118 on the primary trigger support block 120. The primary trigger block 120 includes a plurality of trigger mechanisms 122 each being formed of a trigger arm 124 mounted on a pivot rod (not shown) pivotally movable on upright supports 128 of the trigger support block 120. The front end 131 of the trigger mechanism 122 is formed with a ball holder 130. The ball holder 130 is contoured to contact the exact top of a golf ball when it is properly seated in the groove 116 and against the radiused backstop 118. The ball holder 130 of the trigger arm 124 is biased against the golf ball by a resilient spring or sponge-like material (not shown) placed on the support block 120 at the rear end 125 of the trigger arm 124. Therefore, when the rear end 125 is depressed against the resilient material, the front end 131 of the trigger arm 124 will raise and the golf ball begins to roll down the ramp 112.

The lower, forward (or release) end 160 of the ramp 112 is curved beginning just after the slope-line 134 so as to lie horizontal and parallel to the local horizontal and the putting green surface when the apparatus 110 is in the test position. The curved forward end 160 (i.e. from slope line 134 to the very end of the ramp 112) of the ramp 112 releases the golf balls horizontally to the putting surface thereby eliminating or minimizing bounce as the balls impact the putting green surface.

As with the prior embodiment, at least two level-vials 136, 137 are mounted on the trigger support block 120 and these level vials function in the manner discussed above.

A secondary trigger support block 150 is substantially identical to the primary trigger block 120 but is designed for selective attachment to the ramp 112 at a midway point along therealong. As such, and where the energy of a traditional meter such as that described above is not appropriate when the green configuration is determined, the secondary trigger support block 150 may be secured to the ramp 112 and a "half energy" system may be employed.

With this in mind, the secondary trigger support block 150 includes a U-shaped support to which a plurality of trigger mechanisms 122' substantially identical to that described above is secured. Specifically, each golf ball used in conjunction with the secondary trigger support block 150 sits in one of the radiused rolling grooves 116 and rests against a radiused backstop 118' on the secondary trigger support block 150. Each trigger mechanism 122' is formed of a trigger arm 124' mounted on a pivot rod (not shown) pivotally movable on upright supports 128' of the secondary trigger support block 150. The front end 131' of the trigger mechanism 122' is formed with a ball holder 130'. The ball holder 130' is contoured to contact the exact top of a golf ball when it is properly seated in the groove 116 and against the radiused backstop 118'. The ball holder 130' of the trigger arm 124' is biased against the golf ball by a resilient spring or sponge-like material 123' placed on the secondary trigger support block 150 at the rear end 125' of the trigger arm 124'. Therefore, when the rear end 125' is depressed against resilient material 123' the front end 131' of trigger arm 124' will raise and the golf ball begins to roll down the ramp.

In use, the secondary trigger support block 150 is secured to the track ramp 112 via bolts 142 and is then operated in the manner directed above with reference to the primary support block. The only difference being that prior to performing the measurements, the operator determines whether it is best to use the secondary trigger support block 150 or the primary trigger support block 120 based upon the speed of the green and the appropriate (not highly contoured) putting surface the operator has at hand for measurements. This method is generally achieved by selecting a site on a putting green having a relatively flat surface and determining the extent of putting surface available for measurements, setting up the present green-speed reading apparatus, selecting one of two predetermined start positions for the golf balls based upon the extent of putting surface available for measurements and retaining the golf balls at the selected start position in the golf ball rolling tracks, releasing the golf balls from the start position, allowing the golf balls to roll down the track by gravity onto the putting green surface, measuring the distance the golf balls roll across the putting green from the release end of the ramp, repeating the test with the apparatus facing in the opposite direction at the selected site and measuring the distance the golf balls roll across the putting green from the release end of the ramp, and calculating the average distance of all the golf balls rolled to determine a value in terms of green-speed. As with the prior embodiment, green speed is determined with the help of the calculator 13, although you must multiply the result by two to get the full green speed.

While various preferred embodiments have been shown and described, it will be understood that there is no intent to limit the invention by such disclosure, but rather, is intended to cover all modifications and alternate constructions falling within the spirit and scope of the invention as defined in the appended claims.

What is claimed is:

1. A method of determining the green-speed of a golf putting green, comprising:
    selecting a site on a putting green having a relatively flat surface and determining the extent of putting surface available for measurements;
    setting a green-speed reading apparatus including a ramp, which includes a raised start end and a ground contacting release end with at least one golf ball rolling track thereon, in a first direction whereby the release end of the ramp contacts the putting green surface at the selected site;
    selecting one of two predetermined start positions for a golf ball based upon the extent of putting surface available for measurements and retaining the golf ball at the one of two predetermined start positions in the track;
    releasing the golf ball from the start position, allowing the golf ball to roll down the track by gravity onto the putting green surface;
    measuring the distance the golf ball rolls across the putting green from the release end of the ramp;
    repeating the test with the apparatus facing in the opposite direction at the selected site and measuring the distance the golf ball rolls across the putting green from the release end of the ramp; and
    calculating the average distance of all the golf balls rolled to determine a value in terms of green-speed.

2. The method according to claim 1, wherein the ramp includes a plurality of tracks and the steps of retaining, releasing, measuring and repeating apply to a plurality of golf balls respectively within the plurality of tracks.

3. The method according to claim 1, wherein the releasing step includes releasing a plurality of golf balls and the golf balls are released sequentially.

4. The method according to claim 1, wherein the retaining step is further defined by holding the golf ball at the selected start position with a trigger arm; and, the releasing step is further defined by raising the trigger arm to release the golf ball.

5. The method according to claim 1, wherein the site selecting step is further defined by the step of identifying a site without any cross slopes via the use of a level.

6. The method according to claim 1, further including the step of adjusting and mechanically maintaining the height of the start end of the ramp such that the ramp is at a predetermined angle relative to the local horizontal with the release end of ramp contacting the putting green surface at the selected site.

7. The method according to claim 6, wherein the predetermined angle is 20.2 degrees.

8. An apparatus for measuring the green-speed of a putting green, comprising:
    a golf ball rolling ramp supported above a putting green surface at a selected site and at a selected angle relative to the local horizontal;
    at least one golf ball rolling track extending the entire length of the rolling ramp;
    legs attached to the ball rolling ramp for supporting the ramp at the selected angle;
    a primary trigger support block for the at least one track selectively holding the golf ball and releasing the golf balls down the ramp and onto the putting green surface;
    a secondary trigger support block shaped and dimensioned for selectively attachment at central position along the length of the ramp, the secondary trigger support block selectively holding the golf ball and releasing the golf balls down the ramp and onto the putting green surface.

9. The apparatus according to claim 8, further including a plurality of tracks.

10. The apparatus according to claim 9, wherein each of the plurality of tracks is in the form of a radiused groove shaped and dimensioned for receipt of a golf ball.

11. The apparatus according to claim 10, wherein the grooves are radiused to the diameter size of a standard golf ball.

12. The apparatus according to claim 8, wherein the legs are adjustable in length and pivotally attached to the ramp so as to be foldable thereagainst.

13. The apparatus according to claim 10, wherein the primary trigger support block includes a pivotally mounted trigger arm and a ball holder for holding a golf ball in the same position each time it is placed on the ramp.

14. The apparatus according to claim 13, wherein the secondary trigger support block includes a pivotally mounted trigger arm and a ball holder for holding a golf ball in the same position each time it is placed on the ramp.

15. The apparatus according to claim 14, further including a backstop on the primary trigger support block, the backstop being radiused to the diameter size of a standard golf ball, for holding a golf ball in a fixed position relative to the trigger arm, and a backstop on the secondary trigger support block, the backstop being radiused to the diameter size of a standard golf ball, for holding a golf ball in a fixed position relative to the trigger arm.

16. The apparatus according claim 10, further including a first level-vial preconfigured on the ramp at the selected angle relative to the local horizontal.

17. The apparatus according to claim 16, wherein the selected angle relative to the local horizontal is approximately 20 degrees.

18. The apparatus according to claim 16, further including a second level-vial for determining if cross slopes exist when the apparatus is placed at the selected site.

* * * * *